US011771592B2

(12) United States Patent
Cable, II et al.

(10) Patent No.: US 11,771,592 B2
(45) Date of Patent: Oct. 3, 2023

(54) STABILIZED INTRAOCULAR DRUG DELIVERY SYSTEMS AND METHODS OF USE

(71) Applicants: SpyGlass Pharma, Inc., Aliso Viejo, CA (US); The Regents of the University of Colorado, A body Corporate, Denver, CO (US)

(72) Inventors: Craig Alan Cable, II, Aliso Viejo, CA (US); Malik Y. Kahook, Denver, CO (US); Glenn R. Sussman, Aliso Viejo, CA (US); Sean Maass, Aliso Viejo, CA (US)

(73) Assignees: SpyGlass Pharma, Inc., Aliso Viejo, CA (US); The Regents of the University of Colorado, a body Corporate, Denver, CO (US)

( * ) Notice: Subject to any disclaimer, the term of this patent is extended or adjusted under 35 U.S.C. 154(b) by 0 days.

(21) Appl. No.: 17/947,051

(22) Filed: Sep. 16, 2022

(65) Prior Publication Data

US 2023/0057991 A1 Feb. 23, 2023

Related U.S. Application Data

(63) Continuation of application No. PCT/US2022/038566, filed on Jul. 27, 2022.
(Continued)

(51) Int. Cl.
*A61F 2/16* (2006.01)
*A61F 9/00* (2006.01)

(52) U.S. Cl.
CPC .............. *A61F 9/0017* (2013.01); *A61F 2/16* (2013.01); *A61F 2002/1686* (2013.01); *A61F 2002/16901* (2015.04); *A61F 2250/0067* (2013.01)

(58) Field of Classification Search
CPC .... A61F 9/0017; A61F 2/1613; A61F 2/1648; A61F 2002/16901; A61F 2002/1686
See application file for complete search history.

(56) References Cited

U.S. PATENT DOCUMENTS

2010/0074942 A1 3/2010 Ratner et al.
2015/0209274 A1 7/2015 Venkatraman et al.
(Continued)

FOREIGN PATENT DOCUMENTS

AU 2020267203 B1 4/2021
GB 2586420 A 2/2021

OTHER PUBLICATIONS

Patent Cooperation Treaty, International Search Report and Written Opinion, International Application No. PCT/US2022/038566, dated Jan. 18, 2023, 13 pages.

*Primary Examiner* — William H Matthews
(74) *Attorney, Agent, or Firm* — Polsinelli PC

(57) ABSTRACT

Embodiments disclosed herein generally relate to a stabilized intraocular drug delivery system for implantation into an eye of a subject. The system can include an intraocular lens (IOL) assembly and a drug delivery component. The IOL assembly can include a lens and a haptic. The haptic can include an outer end, an inner end opposite the outer end, a retention tab at the inner end, and a connection tab positioned between the outer end and the inner end and adjoining the lens. The drug delivery component can include at least one therapeutic agent and a fixation portion having an opening to receive the haptic and secure the drug delivery component to the IOL assembly. The fixation portion of the drug delivery component can be secured to the connection tab of the haptic such that the retention tab inhibits movement of the drug delivery component relative to the IOL assembly.

12 Claims, 10 Drawing Sheets

Related U.S. Application Data

(60) Provisional application No. 63/226,507, filed on Jul. 28, 2021.

(56) References Cited

U.S. PATENT DOCUMENTS

2020/0022840 A1* 1/2020 Kahook ................. A61F 2/147
2020/0405538 A1 12/2020 Mandell

* cited by examiner

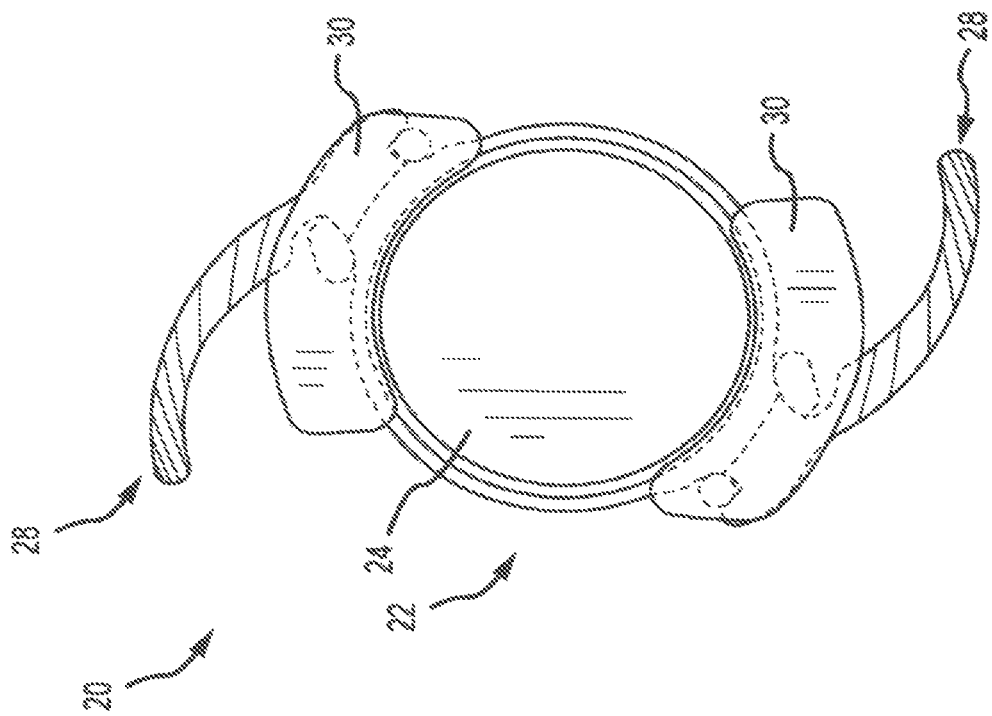
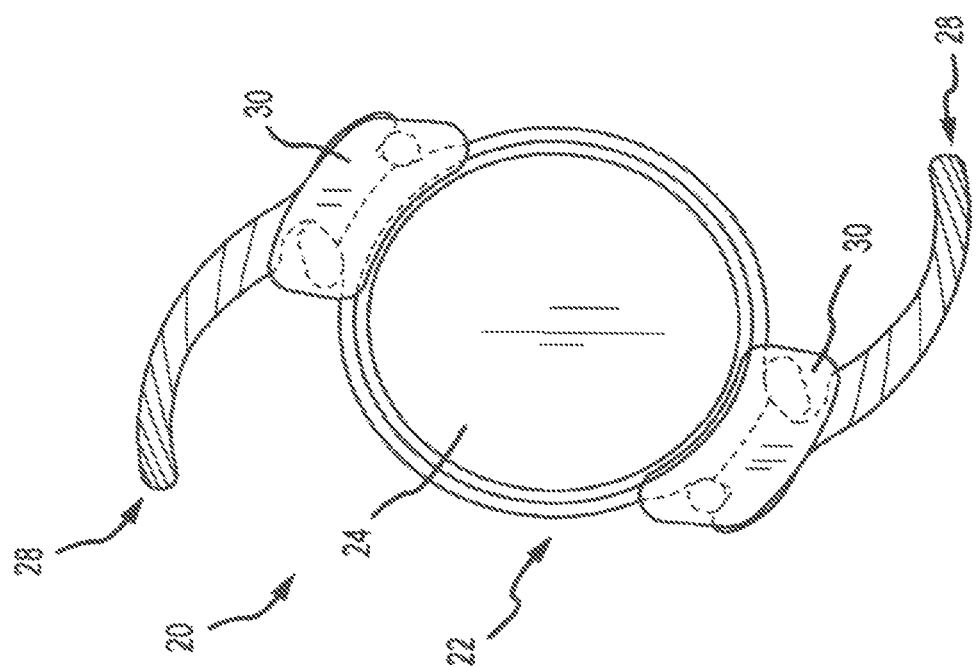
FIG. 3B
FIG. 3A

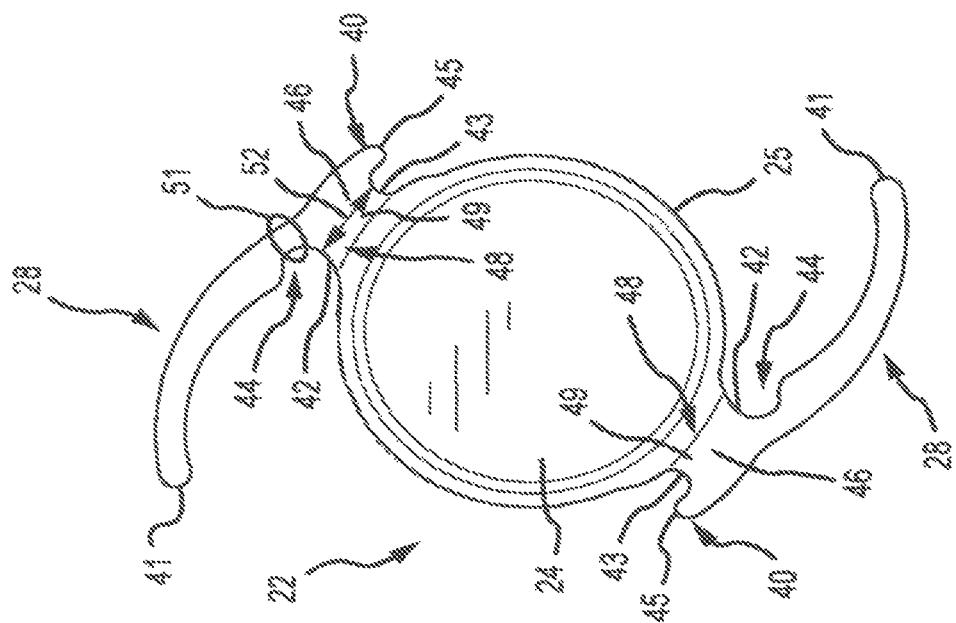
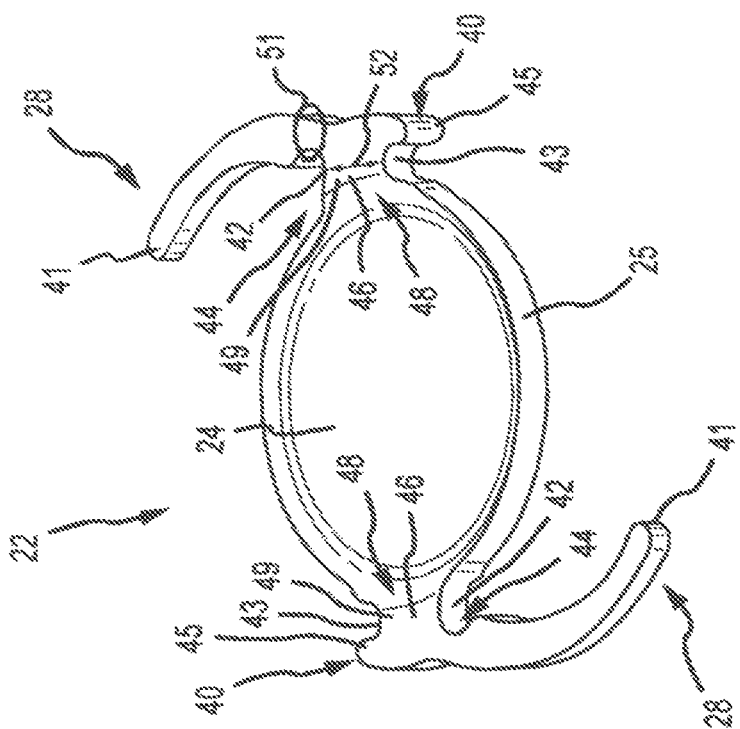

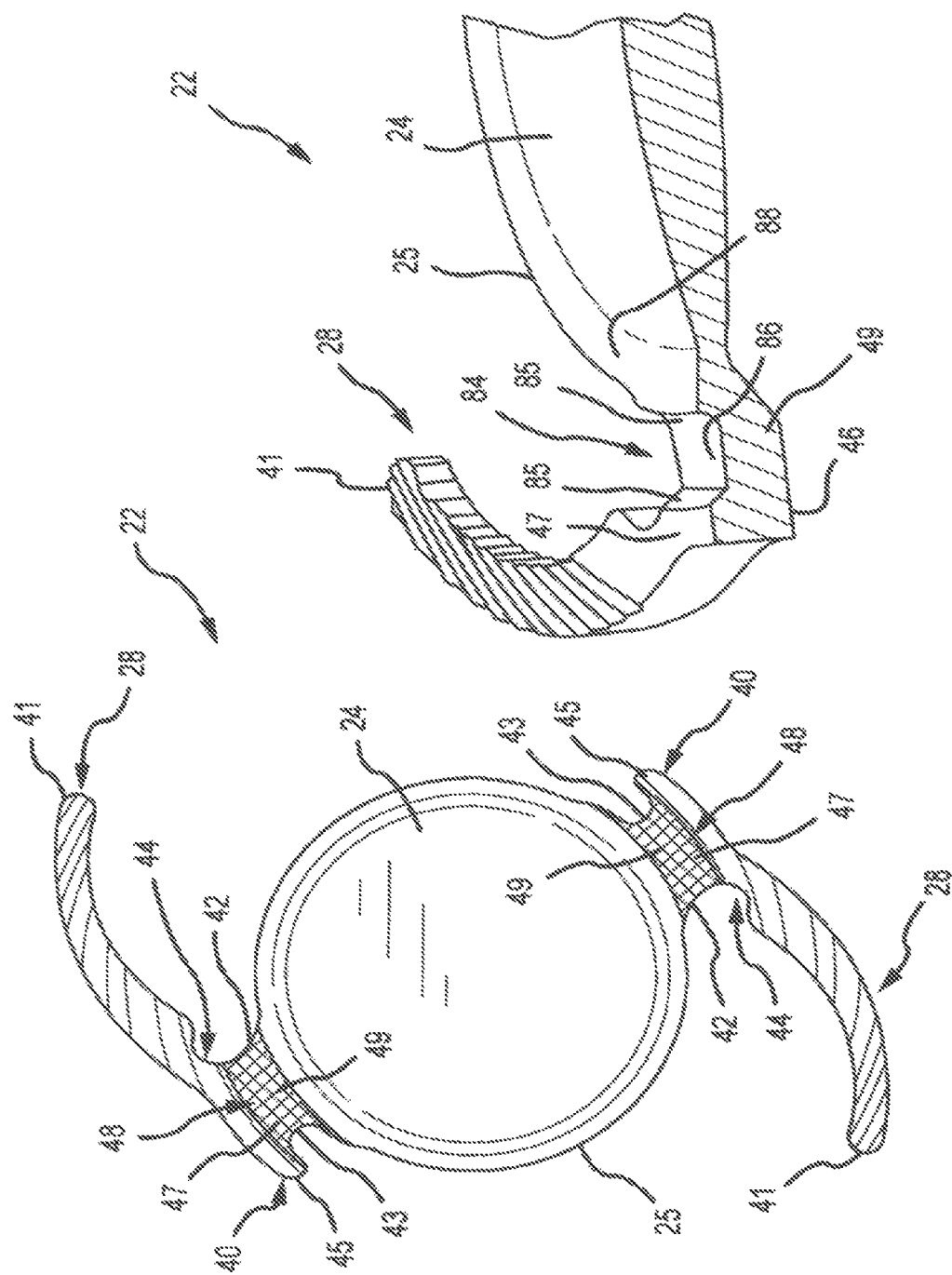

STABILIZED INTRAOCULAR DRUG DELIVERY SYSTEMS AND METHODS OF USE

CROSS-REFERENCE TO RELATED APPLICATIONS

This application is a continuation of International Application No. PCT/US2022/038566, filed Jul. 27, 2022, which claims the benefit of U.S. Provisional Application No. 63/226,507, filed Jul. 28, 2021, each of which is incorporated herein by reference in its entirety for all purposes.

FIELD

The present disclosure relates to the field of intraocular drug delivery systems, implantation and stabilization of intraocular drug delivery systems and methods of use.

BACKGROUND

Intraocular lenses (IOLs) are artificial lenses for the eye that can be implanted to replace the natural lens of a patient's eye after the natural lens is removed. By way of example, a patient's natural lens can be removed because it is affected by cataracts, and an IOL can be implanted to provide clear vision and some degree of focusing to the patient. An intraocular lens can also be implanted in a patient without removing the natural lens (a phakic intraocular lens or PIOL), to correct extreme near-sightedness or far-sightedness.

For example, it can be advantageous to administer therapeutic agents to the eye, coincident with implantation of the IOL, to alleviate various side effects of the IOL or treat other conditions of the eye that might coexist with the conditions that lead to, for example, cataracts and glaucoma. Existing conditions or side-effects of introduction of an IOL such as infection and inflammation can be treated with therapeutic agents incorporated into an IOL or other devices that can be secured to the IOL. In addition to IOLs, ocular implants not including lenses can be implanted to address various conditions.

Previous attempts have disclosed various configurations of drug delivery components to be used in conjunction with IOLs, including the placement of drug delivery components on haptics of IOLs. The devices and methods described below provide for more efficient and/or robust approaches for securing a drug delivery component to an IOL, and related drug delivery systems.

SUMMARY

Certain aspects of the present disclosure include a stabilized intraocular drug delivery system that can be implanted into an eye of a subject. In accordance with these aspects, the system can include an intraocular lens (IOL) assembly and a drug delivery component. The IOL assembly can include a lens and a haptic extending outwardly from the lens. The haptic can engage the drug delivery component, and the haptic can include an outer end, an inner end opposite the outer end, a retention tab at the inner end, and a connection tab positioned between the outer end and the inner end and adjoining the lens. The retention tab can overhang the connection tab. The drug delivery component can include a therapeutic agent and a fixation portion having an opening sized and dimensioned to receive the haptic and secure the drug delivery component to the IOL assembly. The fixation portion of the drug delivery component can be secured to the connection tab of the haptic such that the retention tab inhibits movement or migration of the drug delivery component relative to the IOL assembly.

In certain embodiments, the drug delivery component can further include a drug delivery pad or drug pad including one or more therapeutic agents. The fixation portion can adjoin the drug delivery pad.

In certain embodiments, the fixation portion of the drug delivery component includes a pair of structures and a band. The pair of structures can extend from the drug delivery pad. The pair of structures can be connected by the band to form the opening.

In certain embodiments, when the drug delivery component is secured to the connection tab of the haptic, one of the pair of structures is bordered by the retention tab, a first surface of the connection tab, and a first portion of the lens.

In certain embodiments, the connection tab includes a first surface adjoining the retention tab, and a second surface opposite the first surface. The second surface can adjoin a portion of the haptic. The haptic can further include a gusset formed in the portion of the haptic. The gusset can interface with at least a portion of the drug delivery component to inhibit movement or migration of the drug delivery component relative to the IOL assembly.

In certain embodiments, the portion of the drug delivery component can include one of a pair of structures of the fixation portion.

In certain embodiments, the opening of the fixation portion of the drug delivery component defines a generally rectangular cross-section.

In certain embodiments, the connection tab includes a first surface adjoining the retention tab, and a second surface opposite the first surface. The second surface can adjoin a portion of the haptic. The first and second surfaces can be curvate and define a waist portion. In other embodiments, the waist portion is the narrowest portion of the connection tab.

In some embodiments, the haptic includes a first haptic and a second haptic.

In certain embodiments, the stabilized intraocular drug delivery system can be sized and shaped to be implanted in a capsular bag or the ciliary sulcus of the eye.

Aspects of the present disclosure can include a stabilized intraocular drug delivery system that can be implanted into an eye of a subject. The system can include an intraocular lens (IOL) assembly and a drug delivery component. The IOL assembly can include a lens and a haptic extending outwardly from the lens. The haptic can engage the drug delivery component, and the haptic can include an outer end, an inner end opposite the outer end, and a connection tab positioned between the outer end and the inner end and adjoining the lens. The drug delivery component can include a drug delivery pad and a fixation portion coupled to the drug delivery pad. The drug delivery pad can include one or more therapeutic agents. The fixation portion can include first and second structures extending from the drug delivery pad, a band coupled to the first and second structures, and an opening formed between the drug delivery pad, the first and second structures, and the band. The opening can be sized and dimensioned to receive the haptic and secure the drug delivery component to the IOL assembly. The first and second structures can be differently shaped from each other. The fixation portion of the drug delivery component can be secured to the connection tab of the haptic such that movement or migration of the drug delivery component relative to the IOL assembly is inhibited.

In certain embodiments, the inner end of the haptic is free and overhangs the connection tab.

In certain embodiments, the inner end of the haptic includes a retention tab overhanging the connection tab. The retention tab can include a curvate surface for interfacing with at least one of first and second structures of the fixation portion of the drug delivery component.

In certain embodiments, an axis extends from the first structure, through the band, and to the second structure. The first structure includes a body that is angled relative to the axis.

In certain embodiments, the body of the first structure is oblong.

In certain embodiments, the opening of the fixation portion is generally rectangular in cross-section.

In certain embodiments, the fixation portion can be formed by a polymer or be a polymer.

In certain embodiments, the inner end of the haptic includes a retention tab overhanging the connection tab, the connection tab includes a first surface adjoining the retention tab, and a second surface opposite the first surface. The second surface can adjoin a portion of the haptic. The first and second surfaces can be curvate and define a waist portion. In certain embodiments, the waist portion is the narrowest portion of the connection tab.

In certain embodiments, the haptic includes a first haptic and a second haptic.

In certain embodiments, the stabilized intraocular drug delivery system can be sized and shaped to be implanted in a capsular bag or ciliary sulcus of the eye of the subject.

In certain embodiments, the disclosure relates to intraocular drug delivery systems including an ocular implant and a drug delivery component, where the ocular implant and the drug delivery component are connected in a configuration that stabilizes relative movement of the ocular implant and drug delivery component. In certain embodiments, the ocular implant can be an intraocular lens assembly.

Aspects of the present disclosure can include a stabilized intraocular drug delivery system. In accordance with these aspects, the intraocular drug delivery system includes intraocular lens (IOL) assembly and a drug delivery component. The IOL assembly includes a lens and a haptic extending outwardly from the plane of the lens and configured to engage the drug delivery component, the IOL assembly configured for implantation into an eye of a subject. The drug delivery component includes a therapeutic agent and a fixation portion having an opening sized and dimensioned to receive the haptic and secure the drug delivery component to the IOL assembly. In certain embodiments, the haptic includes a retention tab on the haptic, the retention tab having an outer surface and an inner surface to provide an inner portion at the junction of the haptic to the lens. The haptic further includes a gusset on a surface opposite the inner portion at the junction of the haptic to the optic/lens. In some embodiments, the fixation portion of the drug delivery component, and the retention tab, inner portion, and gusset of the haptic are configured to secure the drug delivery component to the IOL assembly in a manner that stabilizes the relative movement of the ocular implant and drug delivery component.

In some embodiments, attachment of the drug delivery component to the intraocular lens assembly or other intraocular implant can be accomplished through releasable or non-releasable means, and can be accomplished upon manufacture of the IOL assembly, peri-operatively immediately before or after implantation, or intra-operatively, in the same procedure when the IOL assembly is implanted.

In certain embodiments, the drug delivery component can include a first and second drug delivery component, and can be configured to allow for placement of the second drug delivery component into the first drug delivery component. The placement of the second drug delivery component into the first drug delivery component can be accomplished upon manufacture of the IOL assembly, peri-operatively immediately before or after implantation, intra-operatively, or in the same procedure when the IOL assembly is implanted. The first and/or second drug delivery component can be subject to depletion, and upon depletion can be removed and replaced, in an operation that can be accomplished long after the surgery in which the IOL assembly is first inserted.

Aspects of the present disclosure include a stabilized intraocular drug delivery system configured for implantation into an eye of a subject. The system can include an intraocular lens (IOL) assembly and a drug delivery component. The IOL assembly can include a haptic and an optic. The haptic can extend outwardly from the optic at an optic-haptic junction. The haptic can include a pair of indents defining a waist portion at the optic-haptic junction. The drug delivery component can include one or more therapeutic agent(s) and a fixation portion having an opening sized and dimensioned to receive the haptic there through. The fixation portion of the drug delivery component is configured to be secured to the waist portion of the haptic such that movement of the drug delivery component relative to the IOL assembly is inhibited.

In certain embodiments, the pair of indents can be positioned on opposite surfaces from each other. In certain embodiments, each of the pair of indents includes a concave surface.

In certain embodiments, the haptic further includes an outer end, an inner end opposite the outer end, and a retention tab at the inner end. The optic-haptic junction can be positioned between the inner end and the outer end.

In certain embodiments, the retention tab overhangs the waist portion to define one of the pair of indents.

In certain embodiments, the haptic includes a posterior surface, an anterior surface opposite the posterior surface, a first side edge, and a second side edge opposite the first side edge. The first and second side edges can extend between the posterior surface and anterior surface; where a first of the pair of indents is defined on the first side edge and a second of the pair of indents is defined on the second side edge.

In certain embodiments, the fixation portion is formed of a polymer or other suitable material.

In certain embodiments, the drug delivery component further includes a drug delivery pad. In other embodiments, one or more therapeutic agents is included in at least one of the drug delivery pad and the fixation portion. In some embodiments, the drug delivery pad and the fixation portion can include one or more therapeutic agents that are the same or different therapeutic agents.

Aspects of the present disclosure can include a stabilized intraocular drug delivery system configured for implantation into an eye of a subject. The system can include an intraocular lens (IOL) assembly and a drug delivery component. The IOL assembly can include an optic and a haptic extending outwardly from the optic at an optic-haptic junction. The haptic can include an anterior surface, a posterior surface opposite the anterior surface, a first indent on the posterior surface or the anterior surface at the optic-haptic junction. The drug delivery component can include one or more therapeutic agents and a fixation portion having an opening sized and dimensioned to receive the haptic there through. The fixation portion of the drug delivery component is configured to be secured to the haptic at the first indent at the optic-haptic junction such that movement of the drug delivery component relative to the IOL assembly is inhibited.

In certain embodiments, the first indent is on the posterior surface, and the haptic further includes a second indent on the anterior surface.

In certain embodiments, the haptic further includes a first side edge extending between the anterior and posterior surfaces, and a second side edge opposite the first side edge and extending between the anterior and posterior surfaces. The first side edge can include a second indent at the optic-haptic junction, and the second side edge can include a third indent at the optic-haptic junction.

In certain embodiments, the second and third indents each include a concave surface.

In certain embodiments, the haptic further includes an outer end, an inner end opposite the outer end, and a retention tab at the inner end. The optic-haptic junction can be positioned between the inner end and the outer end.

In certain embodiments, the fixation portion is formed of a polymer or other suitable material.

In certain embodiments, the drug delivery component further includes a drug delivery pad, and one or more therapeutic agent(s) is included in at least one of the drug delivery pad and the fixation portion.

BRIEF DESCRIPTION OF THE DRAWINGS

FIGS. 3A and 3B illustrate top views of intraocular drug delivery systems, in accordance with embodiments of the disclosure. FIG. 3A illustrates a smaller drug delivery component attached to an IOL assembly, while FIG. 3B illustrates a larger drug delivery component attached to an IOL assembly.

FIGS. 4A-4D illustrate views of an IOL assembly, in accordance with embodiments of the disclosure. FIGS. 4A and 4B illustrate, respectively, a perspective view and a top view of an IOL assembly having an improved haptic configuration of the disclosure. FIG. 4C illustrates a bottom view of a relief cut out at a haptic-optic juncture of an IOL assembly, while FIG. 4D illustrates a cross-section view of the relief cut of FIG. 4B.

FIG. 6A illustrates a top view of an exemplary intraocular drug delivery system, with cross-section cuts of FIG. 6C and FIG. 6D illustrated. FIG. 6B illustrates a partial side view of the system of FIG. 6A. FIG. 6C and FIG. 6D are partial cross-sections of the system of FIG. 6A, as indicated. FIG. 6E is a partial cross-section of the system in a plane parallel to the plane of the optic/lens.

DETAILED DESCRIPTION OF THE DISCLOSURE

Figure 1:
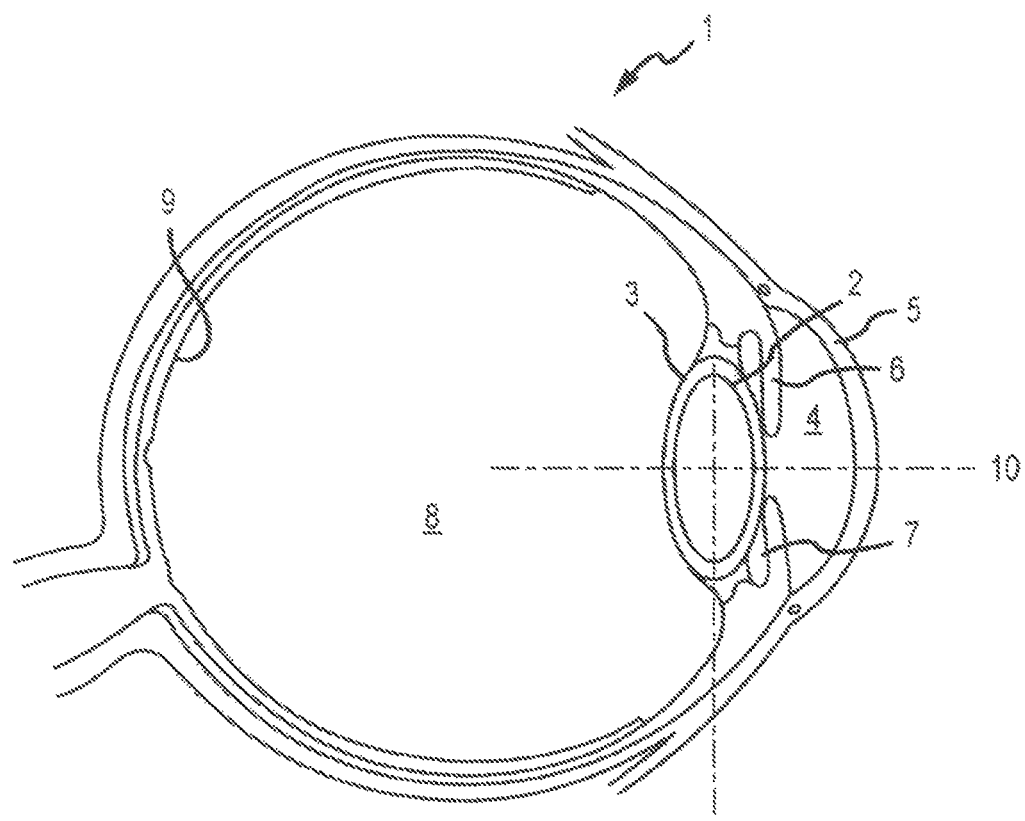
FIGS. 1 and 2 illustrate the environment of use of an intraocular drug delivery system of the disclosure.
Figure 2:
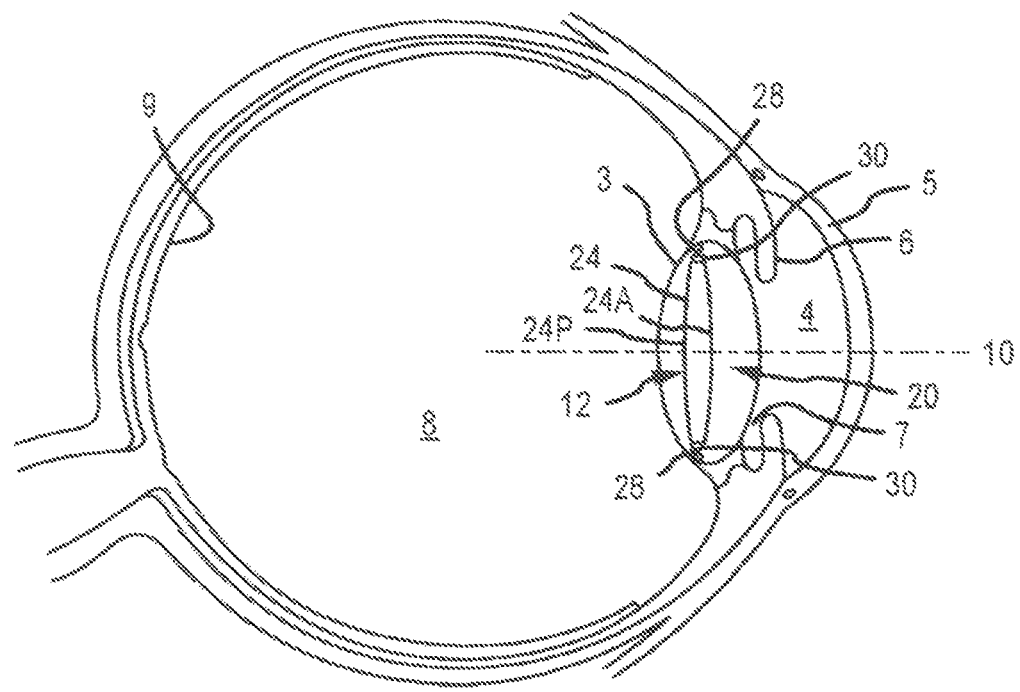

FIGS. 1 and 2 illustrate placement and use of an intraocular drug delivery system in the eye of a patient. The eye 1 includes a lens 2 (the natural lens of the eye) and lens capsular bag 3, and the anterior chamber 4 which includes the cornea 5 and iris 6 and aqueous humour filling the space between the cornea and the iris, and a posterior chamber 7 between the iris and the capsular bag. The posterior cavity/vitreous body 8 is the large space between the lens 2 and the retina 9. The natural lens 2 of the eye 1 is characterized by an optical axis 10. (In the following description of the intraocular drug delivery system, the terms posterior and anterior will be used in relation to the anatomy of the eye, in which the cornea is anterior and the retina is posterior.) FIG. 2 illustrates a placement of the intraocular drug delivery system 20 in the eye including an ocular implant 12 and drug delivery component 30, which is implanted in the capsular bag of a subject (described in more detail herein). The capsular bag can contain the native lens, an artificial lens, or no lens at all.

Certain aspects of the disclosure relate to intraocular drug delivery systems including an ocular implant and a drug delivery component, wherein the ocular implant and the drug delivery component are connected in a configuration that stabilizes relative movement of the ocular implant and drug delivery component. In certain embodiments, the ocular implant 12 can be an intraocular lens (IOL) assembly, which can include an optic/lens 24 at the center and one or more haptics 28 extending outwardly therefrom. The optic/lens 24 includes an anterior side 24A and a posterior side 24P. However, the disclosure is not so limited, and the ocular implant can be any suitable ophthalmic implant configured to include the drug delivery component stabilizing and retaining features described herein.

The intraocular drug delivery systems can include a drug delivery component configured to deliver various therapeutic agents to treat various conditions and disorders of the eye or other disorders capable of being treated by an intraocular drug delivery system. In certain embodiments, the drug delivery component can include one or more therapeutic agents to treat a condition or disorder of the eye. In some embodiments, therapeutic agents useful for the treatment of glaucoma can include, but are not limited to, brimonidine, latanoprost, timolol, pilocarpine, brinzolamide and other therapeutics; for example, beta blockers, alpha agonists, ROCK Inhibitors, adenosine receptor agonists, carbonic anhydrase inhibitors, adrenergic and cholinergic receptor activating agents, prostaglandin analogues, and combinations thereof. In other embodiments, therapeutic agents useful for the treatment of wet macular degeneration glaucoma can include, but are not limited to, aflibercept, bevacizumab, pegaptanib, ranibizumab, steroids, aptamers, and combinations thereof. In yet other embodiments, therapeutic agents useful for the treatment of dry macular degeneration, can include, but are not limited to, complement factors, anti-oxidants, anti-inflammatory agents, and combinations thereof. In other embodiments, the therapeutic agent can be useful in the treatment of uveitis, e.g., methotrexate, antibodies, dexamethasone, triamcinolone, and other steroid agents. The therapeutic agent can also include one or more anti-proliferative agents, anti-mitotic agents, anti-inflammatory agents, and other medications that inhibit or prevent the migration of lens epithelial cells, e.g., to treat posterior capsular opacification. In other embodiments, antibiotics such as fluoroquinolones, non-steroidal agents such as ketorolacs, and steroids such as prednisolones or the like can be incorporated into the drug delivery components for post-op management after cataract or other eye surgery.

Figure 3D:
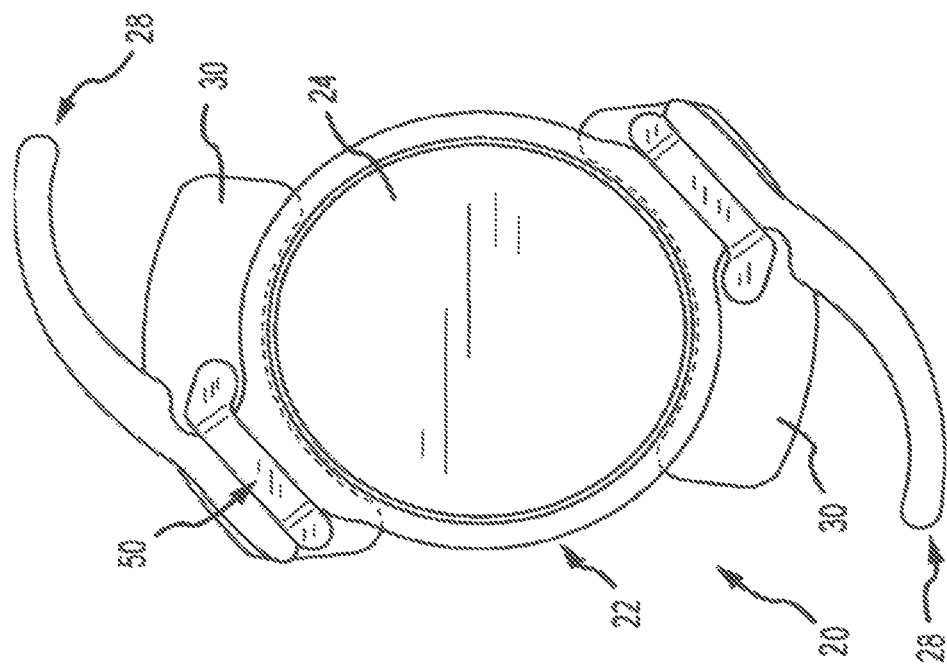
FIGS. 3C-3D illustrate, respectively, a perspective view and a bottom view of the intraocular drug delivery system of FIG. 3B having the larger drug delivery component attached to the IOL assembly.
Figure 3C:
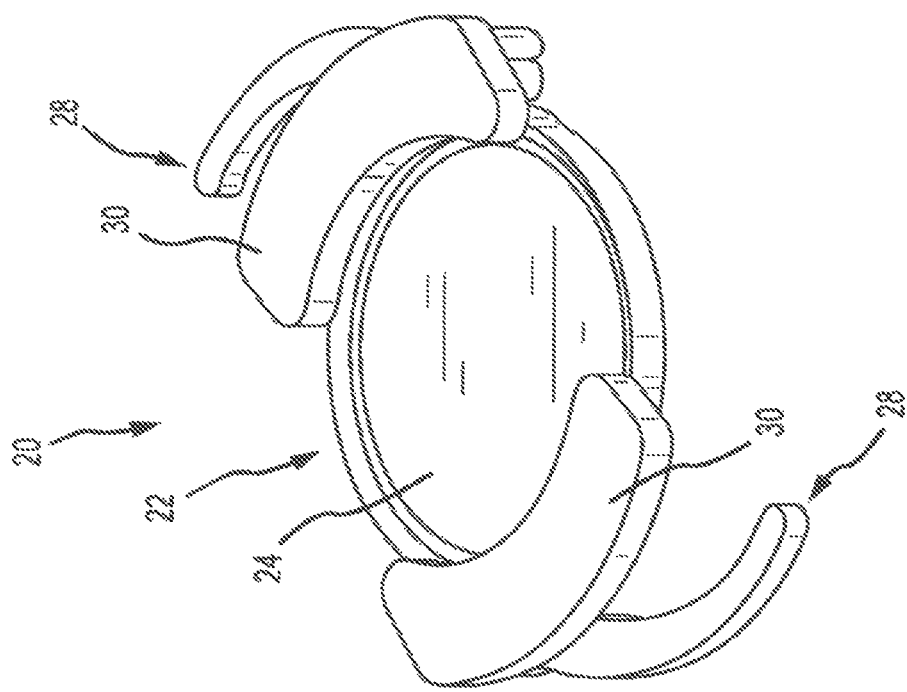

FIGS. 3A and 3B illustrate exemplary intraocular drug delivery systems 20 which can include an IOL assembly 22 and one or more drug delivery components 30. FIGS. 3C and 3D illustrate, respectively, a perspective view showing an anterior side of the system 20 of FIG. 3B and bottom view showing a posterior side of the system 20 of FIG. 3B. In FIG. 3A, the system 20 includes a pair of relatively smaller drug delivery components 30. In FIGS. 3B-3D, the system 20 includes a pair of larger drug delivery components 30. The larger drug delivery components 30 can, for example, elute therapeutic agents for a longer duration or at a higher rate as compared to the smaller drug delivery components 30. The drug delivery components 30 can include different properties; for example, different rates of elution, different therapeutic agents, among other aspects that can be modified. The present disclosure illustrates the relatively larger drug delivery component 30 illustrated in FIGS. 3B-3D. However, the disclosure is not so limited, and the systems and methods described herein are also applicable to the relatively smaller drug delivery component 30 illustrated in FIG. 3A.

The IOL assembly 22 of the system 20 includes an optic/lens 24 at the center and one or more haptics 28 extending outwardly from the plane of optic/lens 24 or a parallel plane. As seen in the figures, the IOL assembly 22 includes a pair of haptics 28 extending outwardly from opposite sides of the optic/lens 24. The optic/lens 24 can include an optic with vision correction or can simply be a scaffold to provide structural support. The drug delivery component 30 is configured for attachment (preferably releasable attachment) to a haptic 28 of the IOL assembly 22. The intraocular drug delivery system 20 includes an anterior side and a posterior side, relative to the eye of the subject when implanted. In other embodiments, the intraocular drug delivery system 20 can optionally include other devices such as a capsular tension ring, or a capsular scaffold for holding the system in place during use.

The outward extent of the haptics 28 are long enough to impinge on the capsular bag of the eye of the subject when the system 20 is implanted, while the radially outward extent of the drug delivery component 30, when installed on the implanted IOL assembly 22, is preferably shorter than that of the haptic 28, so as to avoid impingement of the drug delivery component 30 on the capsular bag in the equatorial region of the capsular bag of the eye of the subject. As shown, FIG. 3A illustrates an embodiment wherein the drug delivery component 30 is configured to dimensionally correspond to the size and shape of the optic-haptic junction area, while FIGS. 3B-3D illustrates an embodiment where the drug delivery component 30 is configured to be dimensionally larger than the optic-haptic junction area. However, the disclosure is not so limited, and the drug delivery component 30 can be sized as shaped in any manner suitable for the intended use, e.g., one-quarter around the circumference of the optic, one-third around the circumference of the optic, one-half around the circumference of the optic, etc.

FIGS. 4A-4D illustrate an exemplary IOL assembly 22 of the disclosure. As illustrated in FIGS. 4A and 4B, each of the haptics 28 includes features to retain and stabilize the drug delivery component (not shown) when coupled to the IOL assembly 22. To that end, each of the haptics 28 includes a retention tab 40 and a gusset 44, which together form a waist or in-cut portion 52 for retaining and stabilizing the fixation portion (not shown) of the drug delivery component when the fixation loop is received in the waist portion 52 (fixation portion 50 of the drug delivery component 30 shown received on the waist portion 52 of IOL assembly 22 in FIG. 3D). The waist portion 52 defines a narrow portion which widens towards the optic/lens 24 and also, widens towards the gusset 44 and retention tab 40. In this way, the drug delivery component is retained at the waist portion 52 such that movement away from the waist portion 52 is inhibited and such that rotation of the drug delivery component relative to the IOL assembly 22 is also inhibited.

Still referring to FIGS. 4A-4B, the haptics have an outer free end 41 and an inner free end 45, both of which are free (i.e., uncoupled to a structure). The outer free end 41 terminates at a rounded nub or tip. The inner free end 45 also terminates at a rounded nub or tip defining the retention tab 40, which overhangs the waist portion 52. The haptics 28 are connected to the optic/lens 24 along a longitudinal length of the haptic 28 at a point or section between the two ends 41, 45. Stated differently, the haptics 28 are not connected to the optic/lens 24 at their terminal ends 41, 45; instead, the ends 41, 45 are free and the haptics 28 are connected to the optic/lens at a point or section in between the ends 41, 45. The haptics 28 are connected to the optic/lens 24 at an optic-haptic junction or lens-haptic junction 48 via a radially extending member or connection tab 49 (hereinafter referred to as "radially extending member") of the haptics 28. The radially extending member 49 is near the inner free end 45 which defines the retention tab 40. The radially extending member 49 extends from an arc or portion of the edge 25 of the optic/lens 24. The radially extending member 49 is defined by a pair of surfaces, a first surface 43 and a second surface 42, that define the waist portion 52. The radially extending member 49 of the haptics 28 and the optic-haptic junction 48 are illustrated in cross-hatching in FIG. 4C and generally refers to the location or position at which the haptic 28 joins the optic/lens 24.

Referring still to FIGS. 4A-4B, opposite the first surface 43 formed by retention tab 40, the haptic 28 includes a curvilinear notch or gusset 44 having the second surface 42 that facilitates flexing and bending of the haptic 28 during use. More particularly, the gusset 44 defines a relatively narrow cross-sectional area 51 of the haptic 28 that permits bending of the haptic 28 between the ends 41, 45. The waist portion 52, in addition to being defined between the second surface 42 and the first surface 43 of the haptic 28, is also defined between an anterior surface 46 and a posterior surface 47 (shown in FIGS. 4C-4D). In some embodiments, the first surface 43 of the retention tab 40 includes a radial or concave surface and the second surface 42 of the retention tab 40 at the gusset 44 includes a radial or concave surface so as to provide a curved or concave inner portion at the optic-haptic junction 48 of the haptic 28 to the lens 24. The anterior surface 46 of the haptic 28, between the retention tab 40 and the gusset 44, can interface with at least a portion of the drug delivery component (not shown) to stabilize its orientation during use. In some embodiments, the anterior surface 46 can be sized and shaped so as to match the size and shape of the drug delivery component (e.g., interface with the entire drug delivery component or substantially the entire drug delivery component).

As illustrated in FIG. 4C, which is a posterior view of the IOL assembly 22, the optic-haptic junction 48 and radially extending member 49 are illustrated with cross-hatching. The radially extending member 49 defining the optic-haptic junction 48 connects the haptic 28 to the optic/lens 24 along a length of the haptic 28 between its terminal ends 41, 45. As illustrated in FIG. 4D, which presents a close-up, cross-sectional view of the IOL assembly 22, the posterior surface 47 of the radially extending member 49 includes a relief cut 84, which provides additional stability to the drug delivery component during use and/or to maintain a PCO barrier. The relief cut 84 is defined by a pair of beveled edges 85 and a recessed surface 86 that lies in a plane that is farther anterior than the optic/lens 24. More particularly, as seen in FIG. 4D, the recessed surface 86 is farther anterior than a rim 88 surrounding the optic/lens 24. In certain embodiments, the recessed surface 86 and the anterior surface 46 can be generally parallel with each other.

As can be understood from the FIGS. 4A and 4B, among others, the waist portion 52 of the haptic 28, at the haptic-optic junction 48, is defined by a pair of indents having concave surfaces 42, 43. The concave surfaces 42, 43 are within the plane of the optic/lens 24. Additionally, the haptic 28 includes the relief cut 84, as seen in FIG. 4D, which defines an indent in the posterior surface 47. Therefore, at the optic-haptic junction 48, the haptic 28 defines an indent on the perimeter of haptic 28 for receiving the drug delivery component thereon. It is noted that the anterior surface 46 of the haptic, as seen in FIG. 4D, can include an indent or relief cut. In one embodiment, the haptic 28 can include indents on the entirety of its perimeter.

Figure 5A:
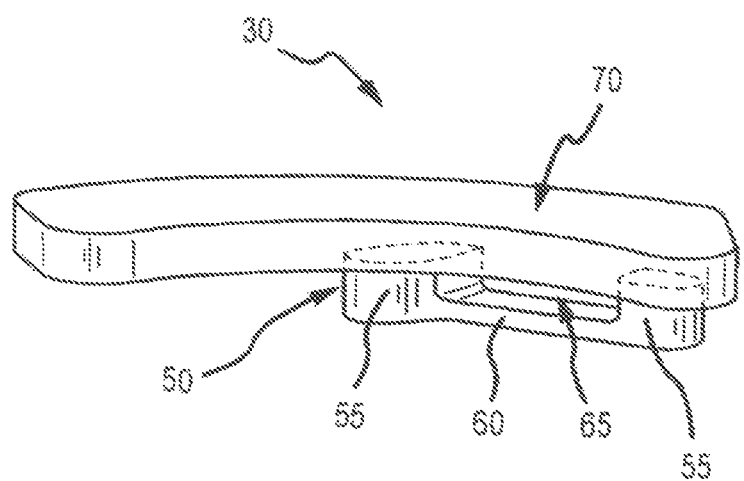
FIGS. 5A-5C illustrate, respectively, a perspective view, a bottom view, and a side view of a drug delivery component, in accordance with embodiments of the disclosure.
Figure 5B:
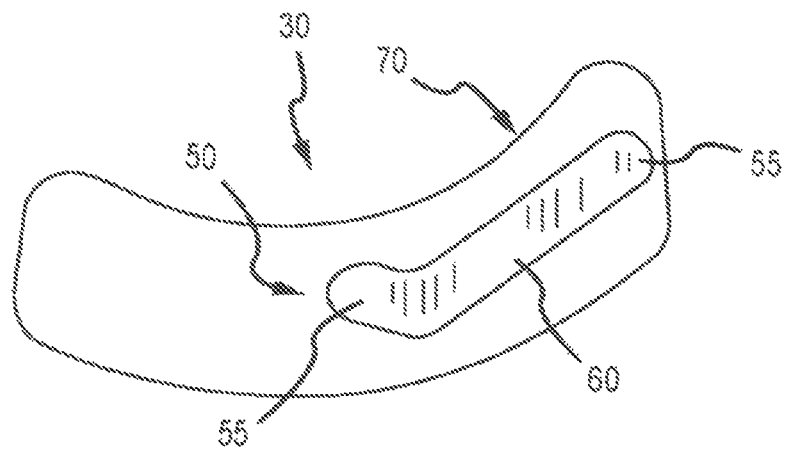
Figure 5C:
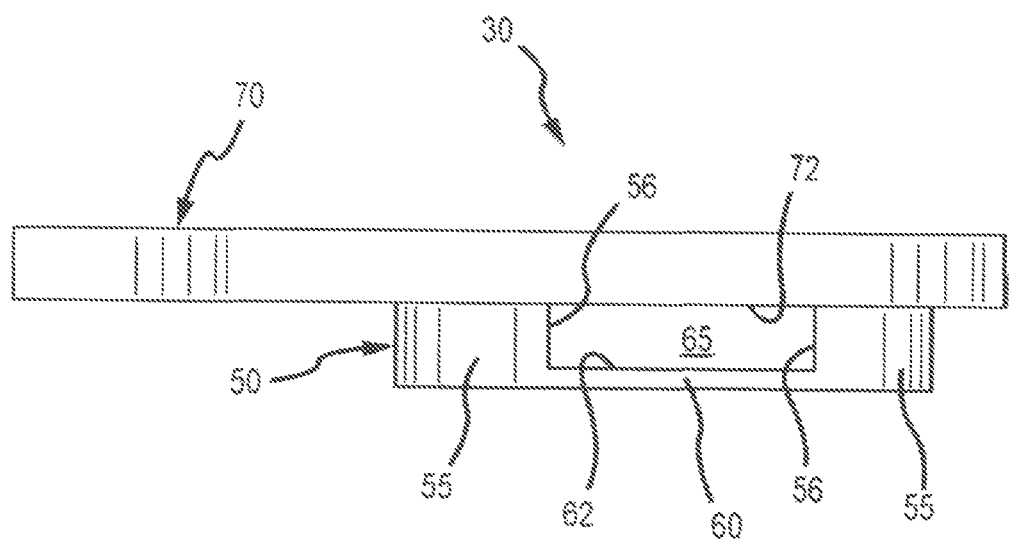

FIGS. 5A through 5C illustrate an exemplary drug delivery component 30 of the intraocular drug delivery system. The drug delivery component 30 can include a therapeutic agent, which can include the entirety of drug delivery pad 70, or a portion thereof (such as an interior drug delivery pad, gel, or drug eluting matrix). The drug delivery pad 70 can elute the one or more therapeutic agent(s) from a drug depot, dissolve or biodegrade over time to release the therapeutic agent, or be formulated in any other suitable drug delivery configuration known in the art. Drug delivery component 30 can further include fixation portion 50 affixed to the posterior side of the drug delivery pad 70. Fixation portion 50 can include structures 55 such as posts which extend vertically from the posterior side of drug delivery pad 70 and are connected by a horizontally extending band 60 to form an opening 65 (e.g., a slot, aperture or compartment). The fixation portion 50 can generally function as a drug delivery component 30 retention loop and can be formed from any suitable materials for the intended use. By way of non-limiting example, the fixation portion 50 can be formed from FDA-approved polymers for ophthalmic use that are compatible with the intended therapeutic agents, e.g., medical grade silicone. Further, the fixation portion 50 can be attached to the drug delivery pad 70 by any method known in the art suitable for such purposes, e.g., medical grade adhesives, thermal bonding, etc. While the drug delivery component 30 is described as including a drug delivery pad 70 that can include one or more therapeutic agent(s), the entirety of the drug delivery component 30, including the drug delivery pad 70 and the fixation portion 50, can include distributed therapeutic agent throughout. The drug delivery pad 70 and fixation portion 50 can include the same or different therapeutic agents therein.

The fixation portion 50 (i.e., retention loop) or a portion thereof can be flexible to permit it to expand over the haptic (not shown) and then contract onto the waist portion of the IOL assembly (not shown). In certain embodiments, the band 60 can be flexible to expand and contract. In certain embodiments, the band 60, and the posts 55 can be flexible to expand and contract. In certain embodiments, the band 60, the posts 55, and the drug delivery pad 70 can be flexible to expand and contract. FIGS. 5A-5C show the drug delivery component 30 in an unexpanded state such as it could exist prior to being coupled with the IOL assembly. FIGS. 6B-6D illustrate the drug delivery component 30 in a state with the band 60 being slightly expanded to stretch over the relief cut on the posterior side of the IOL assembly.

Still referring to FIGS. 5A through 5C, the opening 65 is sized and shaped to receive the haptic of an IOL assembly therein such that the haptic can pass through the opening 65. As best seen in FIG. 5C, the opening 65 generally forms a rectangular cross-section formed by a posterior surface 72 of the drug delivery pad 70, inner surfaces 56 of the posts 55, and an inner surface 62 of the band 60. The surfaces defining the opening 65 generally match or correspond with the shape of the waist portion of the haptic.

Figure 5D:
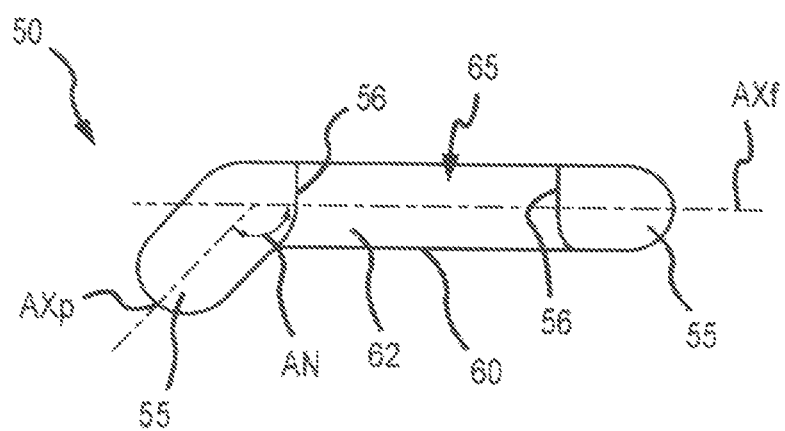
FIG. 5D illustrates a top view of the fixation portion of the drug delivery component with the delivery pad removed from the view, in accordance with embodiments of the present disclosure.

The cross-sectional shape of the posts 55 of the fixation portion 50 of the drug delivery component is illustrated in FIG. 5D, which is a top view of the fixation portion 50 with the delivery pad removed from the view. As seen in the figure, while the opening 65 is generally rectangular in cross-section and sized to receive the haptic therethrough, the outer portions of the posts 55 are sized and shaped to interface with the gusset and retention tab of the haptic (not shown), respectively, to inhibit movement of the drug delivery component relative to the IOL assembly (not shown). The post 55 on the left is oblong or pill shaped and sized to interface with the gusset, and is generally oriented at an angle AN between to an axis AXf of the fixation portion 50 and an axis AXp of the post 55. In certain embodiments, the angle AN can be about 125 degrees. In certain embodiments, the angle AN can be about between about 90 degrees and about 135 degrees.

Figure 6A:
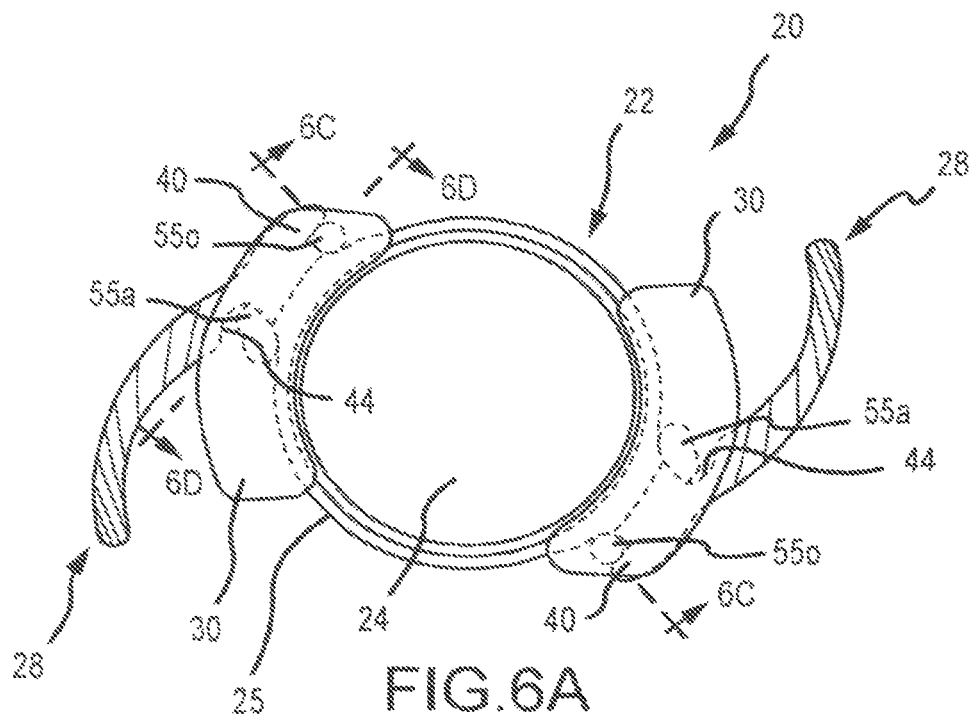
FIGS. 6A-6E illustrate views of an intraocular drug delivery system, in accordance with embodiments of the disclosure.
Figure 6B:
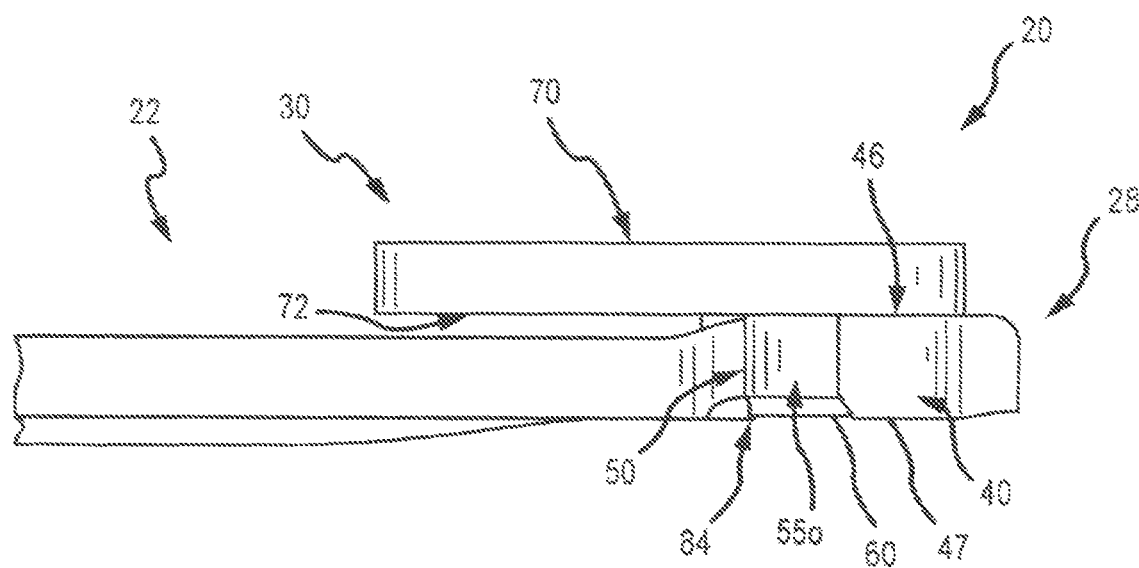
Figure 6C:
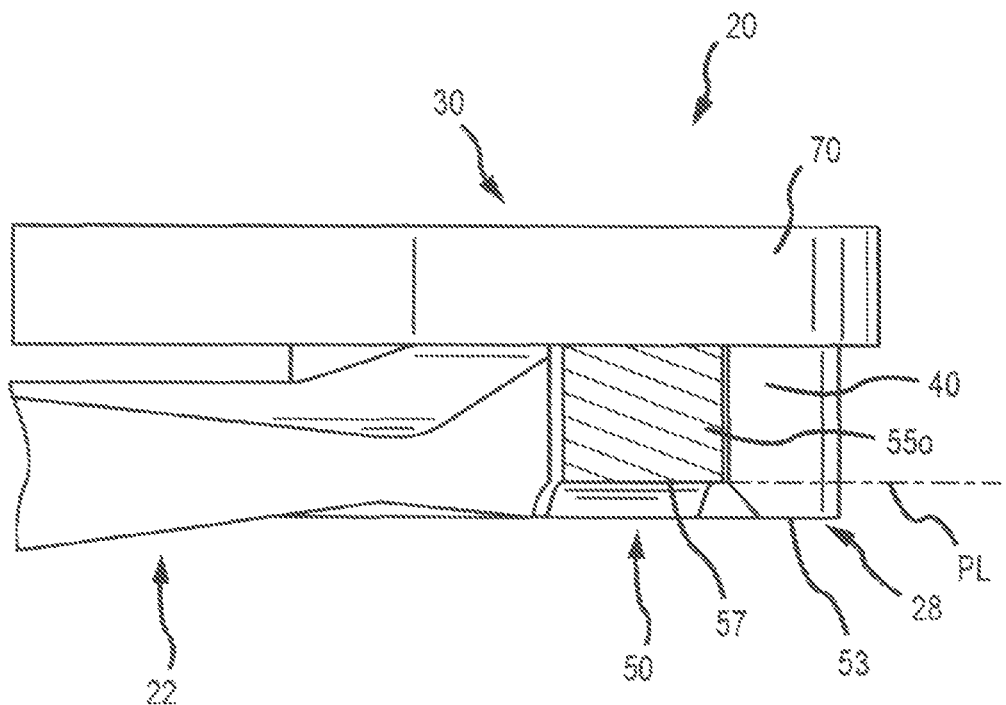
Figure 6D:
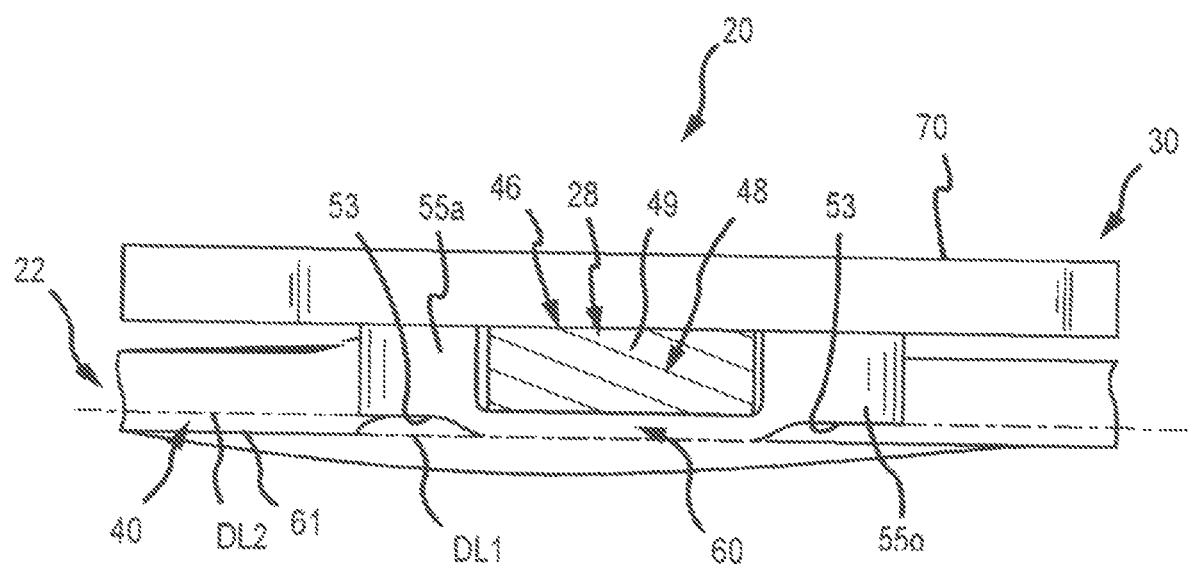
Figure 6E:
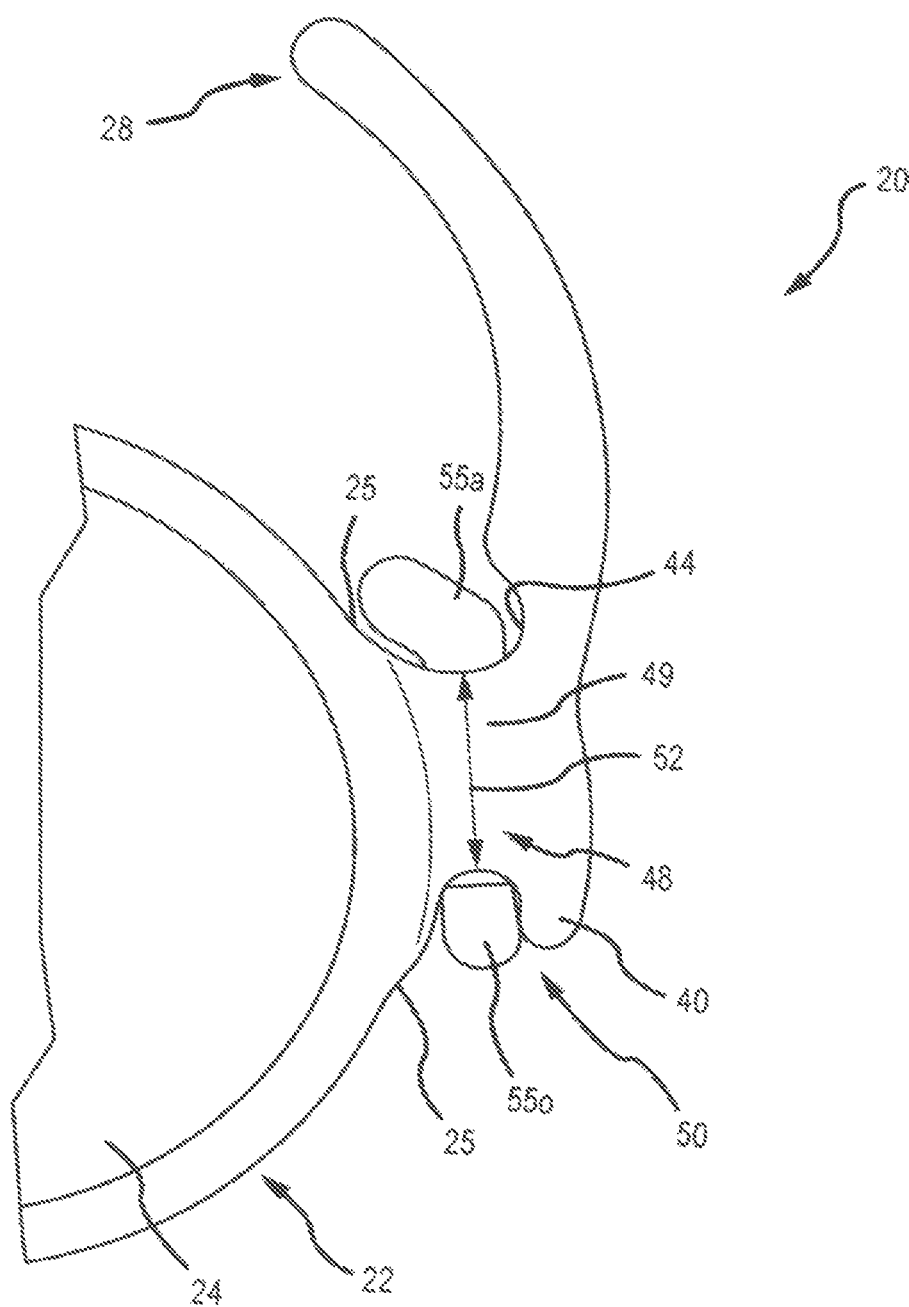

FIG. 6A illustrates a top view of the intraocular drug delivery system 20 with cross-section cuts of FIG. 6C and FIG. 6D illustrated thereon. Similar to FIG. 6A, FIG. 6E illustrates a partial cross-section of the system 20 in a plane parallel to the plane of the optic/lens 24. In FIG. 6A, the drug delivery pad 70 is depicted transparently so as to view the posts 55 relative to the retention tab 40 and gusset 44 of the haptic 28, whereas in FIG. 6E the drug delivery pad is removed from the view via the cross-section. In both figures, the angled or "inside" post 55a is retained between the gusset 44 and the edge 25 of the optic/lens 24 as it transitions into the gusset 44, while the "outer" post 55o is retained between the retention tab 40 and the edge 25 of the optic/lens 24. The cooperation of the retention and stabilization features of the ocular implant and the fixation portion of the drug delivery component provide an intraocular drug delivery system in a configuration that stabilizes relative movement of the ocular implant and drug delivery component.

More specifically, FIG. 6B illustrates a side view of a drug delivery component 30 fitted onto a haptic 28 of an IOL assembly 22 of an embodiment of the disclosure, with the inner or concave portion of retention tab 40 extending about post 55o and at least a portion of the posterior surface 72 of the drug delivery pad 70 positioned on anterior surface 46 of the haptic 28 to provide positional and orientation stabilization to the drug delivery component 30 relative to the IOL assembly 22. The band 60 of the fixation portion 50 is in an extended state and is expanded over the relief cut 84 on the posterior surface 47.

FIG. 6C is a partial cross-sectional image of the system 20 along the section line illustrated on FIG. 6A. In particular, FIG. 6C is a partial cross-sectional image of the system 20 along the section line of the upper left portion of the system 20 of FIG. 6A. FIG. 6C illustrates a cross-section side view of a drug delivery component 30 fitted onto a haptic 28 of an IOL assembly 22 of an embodiment of the disclosure, wherein the bottom surface 57 of post 55o, positioned within the retention tab 40, is higher or more anterior (the plane PL shown by dashed line) than the bottom 53 of the retention tab 40 which provides additional stabilization of the drug delivery component 30 and/or maintains a PCO barrier. The contour of the fixation portion 50 of the drug delivery component 30 relative to the retention and stabilization features of the ocular implant further provide for stabilization of the relative movement of the ocular implant and the drug delivery component 30.

FIG. 6D is a partial cross-sectional image of the system 20 along the section line illustrated on FIG. 6A. FIG. 6D likewise illustrates a cross-section view of a drug delivery component 30 fitted onto the radially extending member 49 of a haptic 28 of an IOL assembly 22 of an embodiment of the disclosure, and illustrates the relative positioning of the fixation portion 50 and the retention and stabilization features of the ocular implant. The cross-section cuts through both posts 55o, 55a, the band 60, and the radially extending member 49 at the optic-haptic junction 48. The horizontal band 60 stretches down and around the radially extending member 49 of the haptic 28 to secure the drug delivery component 30 to the IOL assembly 22. The bottom of the horizontal band 60 is above the posterior capsular opacification (PCO) barrier at the optic-haptic junction (PCO barrier illustrates by the dashed lines DL1). The bottoms 53 of the posts 55o, 55a are higher (the planes shown by the dashed lines DL2) than the bottom 61 of the retention tab 40. Migration or movement, including rotation, of the drug delivery component 30 relative to the haptic 28 is inhibited at least in part by the generally rectangular cross-sectional shape of the radially extending member 49 and the corresponding shape of the fixation portion 50 of the drug delivery component 30.

As described previously, FIG. 6E illustrates a partial cross-section of the system 20 in a plane parallel to the plane of the optic/lens 24. In particular, the drug delivery pad of the drug delivery component (not shown) is removed via the cross-section so only the fixation portion 50 including the posts 55o, 55a are visible. As seen in the figure, the outside post 55o is bordered by the retention tab 40 and an edge 25 of the optic/lens 24, and the angled post 55a is bordered by the gusset 44 and the edge 25 of the optic/lens 24. As such, rotation (i.e., clockwise, counterclockwise in the view of FIG. 6E) of the fixation portion 50 is inhibited. And, since the waist portion 52 of the radially extending member 49 is narrower than the relatively wider portions of the retention tab 40 and gusset 44 on one side and the edges 25 extending outward from the optic/lens 24 side, the fixation portion 50 of the drug delivery component is caused to be stabilized and positionally maintained at the waist portion 52. Therefore, it would entail significant stretching of the fixation portion 50 over the retention tab 40 in order for the drug delivery component to be removed from being positioned over the waist portion 52 of the radially extending member 49.

In certain embodiments, the drug delivery component can include a first and second drug delivery component, and can be configured to allow for placement of the second drug delivery component into the first drug delivery component. The placement of the second drug delivery component into the first drug delivery component can be accomplished upon manufacture of the drug delivery component, peri-operatively immediately before or after implantation, intra-operatively, or in the same procedure when the IOL assembly is implanted. The first and/or second drug delivery component can be subject to depletion, and upon depletion can be removed and replaced, in an operation that can be accomplished long after the surgery in which the IOL assembly is first inserted.

The intraocular drug delivery system can be introduced into the eye of a patient, through a small incision at the edge of the cornea, and into the capsular bag of the patient. For initial installation of the intraocular drug delivery system, the drug delivery component can be fixed to the IOL assembly prior to insertion of both into the eye, and the assembled system can be folded and passed through the incision and then released in the capsular bag or ciliary sulcus. Alternatively, for initial installation of the intraocular drug delivery system, the drug delivery component can be fixed to the IOL assembly after insertion of the IOL into the eye, by first inserting the IOL through the incision and releasing it in the capsular bag or ciliary sulcus, and then inserting the drug delivery component through the incision and manipulating the drug delivery component to slip the fixation portion over the haptic and thereby fix the drug delivery component to the haptic and IOL assembly.

In certain embodiments, when an originally implanted drug delivery component is depleted, either by elution or bio-erosion, a subsequent surgical procedure can be performed in which a surgeon removes the original drug delivery component, making another incision at the border of the cornea to insert and fix a new drug delivery component to the haptic and IOL assembly using a grasping tool. The removal of the original drug delivery component and replacement with a new drug delivery component can be performed, for example, after the original drug delivery component is exhausted or depleted, or whenever it is desired to replace the original drug delivery component with a new drug delivery component which contains a replenished or different therapeutic agent, and can be performed after the incision made to implant the original drug delivery component has healed, and thus requires making a new incision. During the surgical procedure, if necessary, the surgeon can insert a grasping tool to remove the original drug delivery component from the haptic and IOL assembly, and remove it from the eye, and insert a new drug delivery component and use the grasping tool to manipulate the new drug delivery component to slip it over the haptic and thereby secure it to the IOL assembly.

While the preferred embodiments of the devices and methods have been described in reference to the environment in which they were developed, they are merely illustrative of the principles of the inventions. The elements of the various embodiments can be incorporated into each of the other species to obtain the benefits of those elements in combination with such other species, and the various beneficial features can be employed in embodiments alone or in combination with each other. Other embodiments and configurations can be devised without departing from the spirit of the inventions and the scope of the appended claims.

What is claimed is:

1. A stabilized intraocular drug delivery system configured for implantation into an eye of a subject, the stabilized intraocular drug delivery system comprising:
    an intraocular lens (IOL) assembly and a drug delivery component;
    the IOL assembly comprising a lens and a haptic extending outwardly from the lens, the haptic configured to engage the drug delivery component, the haptic comprising an outer end, an inner end opposite the outer end, and a connection tab positioned between the outer end and the inner end and adjoining the lens;
    the drug delivery component comprising a drug delivery pad and a fixation portion coupled to the drug delivery pad, the drug delivery pad including one or more therapeutic agents, the fixation portion including first and second structures extending from the drug delivery pad, a band coupled to the first and second structures, and an opening formed between the drug delivery pad, the first and second structures, and the band, the opening sized and dimensioned to receive the haptic and secure the drug delivery component to the IOL assembly, the first and second structures having different cross-sectional areas from each other; and wherein the fixation portion of the drug delivery component is configured to be secured to the connection tab of the haptic such that movement of the drug delivery component relative to the IOL assembly is inhibited.

2. The stabilized intraocular drug delivery system of claim 1, wherein an axis extends from the first structure, through the band, and to the second structure, and wherein the first structure includes a body that is angled relative to the axis.

3. The stabilized intraocular drug delivery system of claim 2, wherein the body of the first structure is oblong.

4. The stabilized intraocular drug delivery system of claim 1, wherein the inner end of the haptic includes a retention tab overhanging the connection tab, the connection tab includes a first surface adjoining the retention tab, and a second surface opposite the first surface, the second surface adjoining a portion of the haptic, and first and second surfaces being curvate and defining a waist portion, the waist portion being the narrowest portion of the connection tab.

5. A stabilized intraocular drug delivery system configured for implantation into an eye of a subject, the stabilized intraocular drug delivery system comprising:

an intraocular lens (IOL) and a drug delivery component;

the IOL comprising a lens bordered by an edge and a haptic extending outwardly from the edge of the lens at a lens-haptic junction, the haptic comprising, at the lens-haptic junction, first and second indents configured to retain the drug delivery component in a position adjacent the lens and prevent outward movement therefrom, the first indent comprising a first concave surface adjoining the edge of the lens, the second indent comprising a second concave surface adjoining the edge of the lens and positioned opposite of the first concave surface; and the drug delivery component comprising a therapeutic agent and a fixation portion having an opening configured to receive the haptic therethrough, the fixation portion configured to be secured to the first and second indents such that outward movement of the drug delivery component relative to the lens is inhibited.

6. The stabilized intraocular drug delivery system of claim 5, wherein the position of the drug delivery component adjacent the lens is the drug delivery component partly overlaying the edge of the lens.

7. The stabilized intraocular drug delivery system of claim 5, wherein the haptic further comprises an anterior surface, a posterior surface opposite the anterior surface, and a third indent on the posterior surface or the anterior surface at the optic-haptic junction.

8. The stabilized intraocular drug delivery system of claim 5, wherein the drug delivery component further comprises a drug delivery pad, and wherein the therapeutic agent is included in at least one of the drug delivery pad and the fixation portion.

9. The intraocular drug delivery system of claim 5, wherein the fixation portion of the drug delivery component includes a pair of structures and a band, the pair of structures extending from the drug delivery pad, wherein the pair of structures are connected by the band to form the opening.

10. The intraocular drug delivery system of claim 9, wherein, when the fixation portion of the drug delivery component is secured to the first and second indents of the haptic, a first of the pair of structures is partially encircled by the first concave surface and a second of the pair of structures is partially encircled by the second concave surface.

11. The intraocular drug delivery system of claim 9, wherein the pair of structures are of different sizes.

12. The intraocular drug delivery system of claim 5, wherein the first concave surface and the second concave surface are arcuate.

* * * * *